(12) United States Patent
Takahashi

(10) Patent No.: US 12,036,491 B2
(45) Date of Patent: Jul. 16, 2024

(54) AZEOTROPE-LIKE COMPOSITION CONTAINING 1,2-DIFLUOROETHYLENE OR 1,1,2-TRIFLUOROETHYLENE AND HYDROGEN FLUORIDE

(71) Applicant: DAIKIN INDUSTRIES, LTD., Osaka (JP)

(72) Inventor: Kazuhiro Takahashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 337 days.

(21) Appl. No.: 17/385,196

(22) Filed: Jul. 26, 2021

(65) Prior Publication Data

US 2021/0346820 A1  Nov. 11, 2021

Related U.S. Application Data

(63) Continuation of application No. PCT/JP2020/002790, filed on Jan. 27, 2020.

(30) Foreign Application Priority Data

Jan. 28, 2019 (JP) .............................. 2019-012369
Jul. 1, 2019 (JP) .............................. 2019-123244

(51) Int. Cl.
*B01D 3/14* (2006.01)
*B01D 3/00* (2006.01)
(Continued)

(52) U.S. Cl.
CPC ............... *B01D 3/36* (2013.01); *C01B 7/196* (2013.01)

(58) Field of Classification Search
CPC ........ C07C 21/18; C07C 17/383; C01B 7/191
(Continued)

(56) References Cited

U.S. PATENT DOCUMENTS

2012/0261252 A1* 10/2012 Knapp .................. C07C 17/386
 203/67
2014/0077123 A1  3/2014 Fukushima
(Continued)

FOREIGN PATENT DOCUMENTS

CN   102015593   4/2011
CN   104837951   8/2015
(Continued)

OTHER PUBLICATIONS

International Search Report issued Apr. 28, 2020 in International (PCT) Application No. PCT/JP2020/002790.
(Continued)

*Primary Examiner* — Monzer R Chorbaji
(74) *Attorney, Agent, or Firm* — WENDEROTH, LIND & PONACK, L.L.P.

(57) ABSTRACT

This disclosure provides a novel azeotrope-like composition and a separation method using the composition. The disclosure provides an azeotrope-like composition comprising 1,2-difluoroethylene (HFO-1132) and hydrogen fluoride; an azeotrope-like composition comprising 1,1,2-trifluoroethylene (HFO-1123) and hydrogen fluoride; and a separation method of a composition comprising hydrogen fluoride and at least one member selected from the group consisting of trans-1,2-difluoroethylene (HFO-1132(E)), cis-1,2-difluoroethylene (HFO-1132(Z)), and 1,1,2-trifluoroethylene (HFO-1123).

5 Claims, 1 Drawing Sheet

(51) Int. Cl.
    *B01D 3/34*     (2006.01)
    *B01D 3/36*     (2006.01)
    *C01B 7/19*     (2006.01)

(58) Field of Classification Search
    USPC ........................................ 203/50, 62, 81, 87
    See application file for complete search history.

(56) References Cited

U.S. PATENT DOCUMENTS

| | | | |
|---|---|---|---|
| 2015/0322321 A1 | 11/2015 | Deur-Bert et al. | |
| 2016/0046548 A1* | 2/2016 | Bonnet | C09K 3/30 |
| | | | 252/182.12 |
| 2018/0002585 A1 | 1/2018 | Fukushima | |
| 2019/0330507 A1 | 10/2019 | Fukushima | |

FOREIGN PATENT DOCUMENTS

| | | |
|---|---|---|
| EP | 2 993 212 | 3/2016 |
| JP | 2011-513227 | 4/2011 |
| JP | 2016-23145 | 2/2016 |
| JP | 2016-519090 | 6/2016 |
| WO | 2009/010472 | 1/2009 |
| WO | 2009/105512 | 8/2009 |
| WO | 2009/105517 | 8/2009 |
| WO | 2012/157765 | 11/2012 |

OTHER PUBLICATIONS

International Preliminary Report on Patentability issued Jul. 27, 2021 in corresponding International Patent Application No. PCT/JP2020/002790.

Extended European Search Report dated Oct. 6, 2022 in corresponding European Patent Application No. 20748120.1.

* cited by examiner

AZEOTROPE-LIKE COMPOSITION CONTAINING 1,2-DIFLUOROETHYLENE OR 1,1,2-TRIFLUOROETHYLENE AND HYDROGEN FLUORIDE

TECHNICAL FIELD

The present disclosure relates to an azeotrope-like composition comprising 1,2-difluoroethylene or 1,1,2-trifluoroethylene and hydrogen fluoride, and a separation method of hydrogen fluoride using the composition.

BACKGROUND ART

Working media for heat cycles characterized by comprising 1,2-difluoroethylene (HFO-1132) are known. It is disclosed that these working media have less impact on the ozone layer and on global warming since HFO-1132 contained in the media have a carbon-carbon double bond, which is easily decomposed by OH radicals in the air (Patent Literature (PTL) 1).

A known method for producing 1,1,2-trifluoroethylene (HFO-1123) comprises dehydrofluorination of 1,1,1,2-tetrafluoroethane (PTL 2).

CITATION LIST

Patent Literature

PTL 1: WO2012/157765
PTL 2: WO2009/010472

SUMMARY

Solution to Problem

Item 1. An azeotrope-like composition comprising 1,2-difluoroethylene (HFO-1132) and hydrogen fluoride.

Advantageous Effects

The present disclosure provides a novel azeotrope-like composition and a separation method that uses the composition.

DESCRIPTION OF EMBODIMENTS

Figure 1:
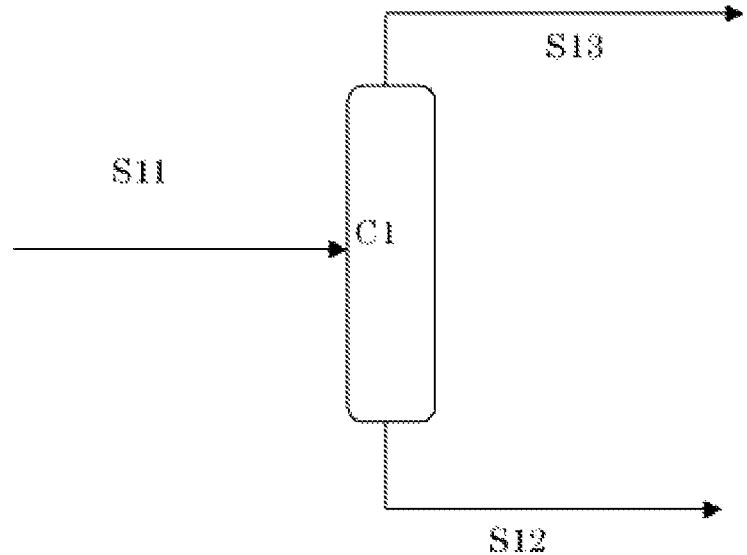
FIG. 1 is a diagram showing an example of a separation method that uses an azeotrope-like composition.

In the present specification, the term "azeotrope-like composition" refers to a composition that can be treated substantially as an azeotropic composition. More specifically, the term "azeotrope-like composition" as used herein refers to a constant boiling mixture or a substantially constant boiling mixture of two or more substances that behave substantially as a single substance. One of the characteristics of azeotrope-like compositions is that the formulation of vapor generated by evaporation or distillation of the liquid substantially does not undergo a change from the formulation of the liquid. That is, in the present specification, a mixture that boils, distills, or refluxes without substantial change in formulation is referred to as an "azeotrope-like composition." More specifically, in the present disclosure, a composition is defined as an azeotrope-like composition when the difference between the bubble point vapor pressure of the composition and the dew point vapor pressure of the composition at a specific temperature is 3% or less (based on the bubble point pressure).

Examples of a method for producing 1,2-difluoroethylene (HFO-1132) include a production method comprising dehydrofluorination of 1,1,2-trifluoroethane (HFC-143).

The present inventor focused on the fact that trans-1,2-difluoroethylene (HFO-1132(E)), cis-1,2-difluoroethylene (HFO-1132(Z)), and 1,1,2-trifluoroethylene (HFO-1123) obtained by a conventional method contain hydrogen fluoride as a by-product, which must be separated.

The inventor found that combinations of these target products and hydrogen fluoride form azeotrope-like compositions, and further found that these compositions are useful in separation based on a method such as distillation, extraction, or liquid-liquid separation. The present disclosure has thus been completed.

1. Composition 1

Composition 1 is an azeotrope-like composition comprising 1,2-difluoroethylene (HFO-1132) and hydrogen fluoride (HF).

HFO-1132 has structural isomers, i.e., HFO-1132(E) and HFO-1132(Z). In the present specification, HFO-1132 comprises HFO-1132(E) and/or HFO-1132(Z), unless otherwise specified. In composition 1, HFO-1132 for use may be HFO-1132(E) alone, HFO-1132(Z) alone, or a mixture of HFO-1132(E) and HFO-1132(Z). HFO-1132 is preferably HFO-1132(E) or HFO-1132(Z).

In terms of efficient separation, composition 1 comprises HFO-1132 in an amount of preferably 50 mass % or more and less than 100 mass %, and more preferably 80 mass % or more and less than 100 mass %, based on the total amount of HFO-1132 and hydrogen fluoride, defined as 100 mass %.

At a temperature of 40° C., composition 1 becomes an azeotrope-like composition when it comprises 99 mass % or more and less than 100 mass % of HFO-1132, based on the total amount of HFO-1132 and hydrogen fluoride, defined as 100 mass %; and becomes an azeotrope-like composition when it comprises 97 mol % or more and less than 100 mol % of HFO-1132, based on the total amount of HFO-1132 and hydrogen fluoride, defined as 100 mol %.

When HFO-1132 is HFO-1132(E), composition 1 preferably has a boiling point of −40° C. to 40° C. at a pressure of 185 kPa to 2480 kPa, and more preferably has a boiling point of −30° C. to 30° C. at a pressure of 279 kPa to 1850 kPa.

Further, when HFO-1132 is HFO-1132(Z), composition 1 preferably has a boiling point of −40° C. to 40° C. at a pressure of 51 kPa to 1880 kPa, and more preferably has a boiling point of −30° C. to 30° C. at a pressure of 83 kPa to 691 kPa.

Composition 1 can be an azeotrope-like composition at the above range of temperature and pressure.

In the present specification, the term "pressure" refers to absolute pressure, unless otherwise specified.

Composition 1 may further comprise an additional compound in addition to HFO-1132 and hydrogen fluoride.

The additional compound is not limited and can be broadly selected as long as it does not interfere with composition 1 becoming an azeotrope-like composition. The additional compounds may be used singly, or in a combination of two or more.

Examples of the additional compound include additional compound 1 and additional compound 2.

Examples of additional compound 1 include 1,1-difluoroethylene (HFO-1132a), 1,1,2-trifluoroethylene (HFO-1123), fluoromethane (HFC-41), 1,1,2,2-tetrafluoroethane (HFC-134), and 1,1,2-trifluoroethane (HFC-143).

Examples of additional compound 2 include E-1-chloro-2-fluoroethylene (HCFO-1131(E)), Z-1-chloro-2-fluoroethylene (HCFO-1131(Z)), 1,1,1-trifluoroethane (HFC-143a), 1,1-difluoroethane (HFC-152a), fluoroethane (HFC-161), 2-chloro-1,1,1-trifluoroethane (HCFC-133a), 1-chloro-1,1,2-trifluoroethane (HCFC-133), 2,2-dichloro-1,1,1-trifluoroethane (HCFC-123), and 1,2-difluoroethane (HFC-152).

The additional compound is preferably additional compound 1 since it is more useful when formed into a composition. Specifically, the additional compound is preferably at least one member selected from the group consisting of 1,1-difluoroethylene (HFO-1132a), 1,1,2-trifluoroethylene (HFO-1123), fluoromethane (HFC-41), 1,1,2,2-tetrafluoroethane (HFC-134), and 1,1,2-trifluoroethane (HFC-143).

When additional compound 1 is contained as the additional compound, additional compound 1 is preferably contained in a total amount of more than 0 mass % and 15 mass % or less, and more preferably more than 0 mass % and 10 mass % or less, based on the entire composition 1 defined as 100 mass %.

When additional compound 2 is contained as the additional compound, additional compound 2 is preferably contained in a total amount of more than 0 mass % and 1 mass % or less, more preferably more than 0 mass % and 0.5 mass % or less, and even more preferably more than 0 mass % and 0.1 mass % or less, based on the entire composition 1 defined as 100 mass %.

Furthermore, when both additional compound 1 and additional compound 2 are contained as the additional compound, it is preferred that additional compound 1 satisfies the above total amount of additional compound 1, and that additional compound 2 satisfies the above total amount of additional compound 2.

Composition 1 can serve as an important composition when azeotropic distillation of a mixture of HFO-1132 and HF is performed to separate HF from HFO-1132.

For example, HF can be separated from HFO-1132 by extracting an azeotrope-like composition that comprises HFO-1132 and HF from a composition that comprises at least HFO-1132 and HF by azeotropic distillation.

The azeotropic distillation is a method of concentration or separation of a target product by operating a distillation column under conditions in which an azeotropic or azeotrope-like composition is separated. In some cases, azeotropic distillation can allow distillation of only the target component for separation. In other cases, however, azeotropic distillation occurs only when another component that forms an azeotropic mixture with one or more of the target components for separation is added from the outside. In the present specification, both the former and the latter cases are referred to as "azeotropic distillation."

2. Composition 2

Composition 2 is an azeotrope-like composition comprising 1,1,2-trifluoroethylene (HFO-1123) and hydrogen fluoride (HF).

In terms of efficient separation, composition 2 comprises HFO-1123 in an amount of preferably 50 mass % or more and less than 100 mass %, and more preferably 80 mass % or more and less than 100 mass %, based on the total amount of HFO-1123 and hydrogen fluoride, defined as 100 mass %.

At a temperature of 40° C., composition 2 becomes an azeotrope-like composition when it comprises 99 mass % or more and less than 100 mass % of HFO-1123, based on the total amount of HFO-1123 and hydrogen fluoride, defined as 100 mass %; and becomes an azeotrope-like composition when it comprises 97 mol % or more and less than 100 mol % of HFO-1123, based on the total amount of HFO-1123 and hydrogen fluoride, defined as 100 mol %.

Composition 2 preferably has a boiling point of −40° C. to 40° C. at a pressure of 249 kPa to 3480 kPa, and more preferably has a boiling point of −30° C. to 30° C. at a pressure of 372 kPa to 2375 kPa. Composition 2 can be an azeotrope-like composition at the above range of temperature and pressure.

Composition 2 may further comprise an additional compound in addition to HFO-1123 and hydrogen fluoride.

The additional compound is not limited, and can be broadly selected as long as it does not interfere with composition 2 becoming an azeotrope-like composition. The additional compounds may be used singly, or in a combination of two or more.

Examples of the additional compound include E-1-chloro-2-fluoroethylene (HCFO-1131(E)), Z-1-chloro-2-fluoroethylene (HCFO-1131(Z)), 1,1,1-trifluoroethane (HFC-143a), 1,1-difluoroethylene (HFO-1132a), 1,1-difluoroethane (HFC-152a), fluoroethane (HFC-161), 1,1,2-trifluoroethane (HFC-143), 2-chloro-1,1,1-trifluoroethane (HCFC-133a), 1-chloro-1,1,2-trifluoroethane (HCFC-133), 2,2-dichloro-1,1,1-trifluoroethane (HCFC-123), and 1,2-difluoroethane (HFC-152).

The total amount of the additional compound contained may be appropriately selected within the range in which it does not interfere with composition 2 becoming an azeotrope-like composition.

When the additional compound is contained, the total amount thereof is preferably more than 0 mass % and 1 mass % or less, more preferably more than 0 mass % and 0.5 mass % or less, and even more preferably more than 0 mass % and 0.1 mass % or less, based on the entire composition 2 defined as 100 mass %.

Composition 2 can serve as an important composition when azeotropic distillation of a mixture of HFO-1123 and HF is performed to separate HF from HFO-1123.

For example, HF can be separated from HFO-1123 by extracting an azeotrope-like composition that comprises HFO-1123 and HF from a composition that comprises at least HFO-1123 and HF by azeotropic distillation.

3. Separation Method

The present disclosure also discloses a separation method of each component using the composition described above.

The separation method according to the present disclosure is a separation method of a composition comprising hydrogen fluoride and at least one member selected from the group consisting of trans-1,2-difluoroethylene (HFO-1132(E)), cis-1,2-difluoroethylene (HFO-1132(Z)), and 1,1,2-trifluoroethylene (HFO-1123), the method comprising steps (a) and (b), and optionally further comprising step (c):

(a) supplying a composition comprising hydrogen fluoride and at least one member selected from the group consisting of HFO-1132(E), HFO-1132(Z), and HFO-1123 to a first distillation column;

(b) obtaining, as a first distillate, an azeotrope-like composition comprising hydrogen fluoride and at least one member selected from the group consisting of HFO-1132(E), HFO-1132(Z), and HFO-1123, and extracting, as a bottom composition of the first distillation column, a composition that is more enriched in either i) at least one member selected from the group consisting of HFO-1132(E), HFO-1132(Z), and HFO-1123, or ii)

hydrogen fluoride, in terms of the concentration, than the supplied composition; and (c) supplying the first distillate to a second distillation column to perform distillation in the second distillation column under a pressure different from that of the first distillation column.

In the separation method, the composition comprising hydrogen fluoride and at least one member selected from the group consisting of HFO-1132(E), HFO-1132(Z), and HFO-1123 as a starting composition for use in step (a) may be a composition consisting of hydrogen fluoride and at least one member selected from the group consisting of HFO-1132 (E), HFO-1132(Z), and HFO-1123, or may be a composition further comprising other components in addition to hydrogen fluoride and at least one member selected from the group consisting of HFO-1132(E), HFO-1132(Z), and HFO-1123.

In step (b) above, the concentration of either i) or ii) in the composition obtained after the first distillate has been distilled from the supplied composition is higher than the concentration in the supplied composition (because the total amount and the formulation of the composition undergo a change). The composition that is more enriched in either i) or ii) in tams of the concentration than the supplied composition is extracted as the bottom composition of the first distillation column.

In the separation method described above, step (c) is not an essential step and is optional. The separation method may be a method that consists of steps (a) and (b) above, a method that consists of steps (a) to (c) above, or a method that further comprises other steps in addition to steps (a) to (c) above.

The operating conditions for each of the first and second distillation columns can be appropriately set. In terms of the efficiency of distillation and the like, the operating conditions for the second distillation column are preferably different from those for the first distillation column.

Figure 2:
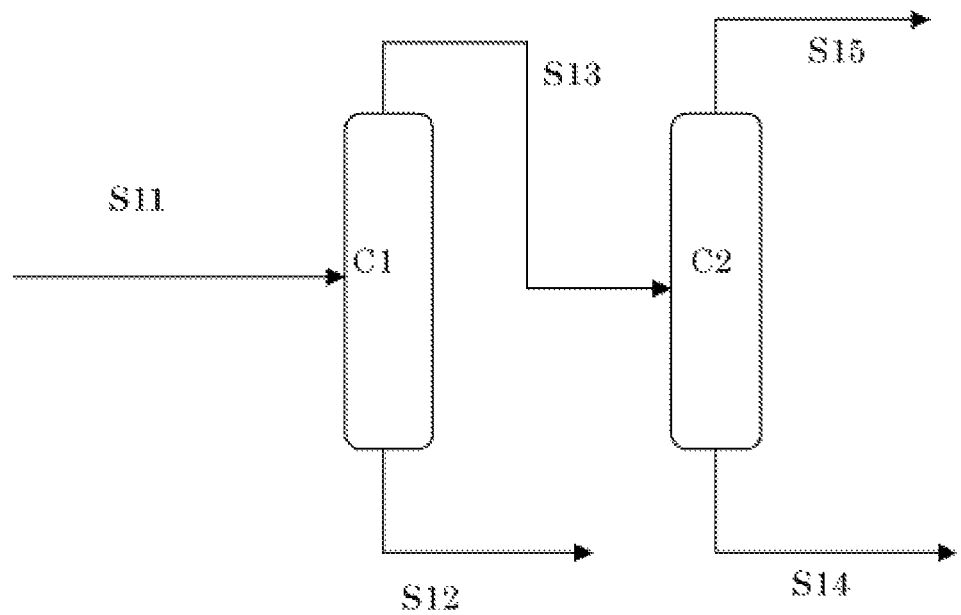
FIG. 2 is a diagram showing another example of a separation method that uses an azeotrope-like composition.

FIG. 1 is a diagram showing an example of the separation method, and FIG. 2 is a diagram showing another example.

In FIG. 1, C1 represents a first distillation column. As shown in FIG. 1, a composition is supplied from S11 to C1, the bottom composition of the first distillation column is extracted from S12, and the first distillate is obtained from S13.

In FIG. 2, C1 represents a first distillation column, and C2 represents a second distillation column. As shown in FIG. 2, a composition is supplied from S11 to C1, the bottom composition of the first distillation column is extracted from S12, the first distillate obtained from S13 is supplied to C2, the bottom composition of the second distillation column is extracted from S14, and the second distillate is obtained from S15. For example, the operating pressure of the second distillation column may be set to be different from that of the first distillation column to thus change the separation properties in each distillation column, whereby HF, which could not be separated in the first distillate, can be extracted as the bottom composition of the second distillation column, and HFO-1132 and/or HFO-1123 of even higher purity can be obtained as the second distillate. The pressure range in each distillation column is appropriately set within the pressure range in which HFO-1132 and HFO-1123 each become azeotrope-like compositions. For HFO-1132(E), the pressure is preferably 185 kPa to 2480 kPa. For HFO-1132(Z), the pressure is preferably 51 kPa to 1880 kPa. For HFO-1123, the pressure is preferably 249 kPa to 3480 kPa.

The separation method above is a separation method comprising separating a composition that comprises hydrogen fluoride and at least one member selected from the group consisting of HFO-1132(E), HFO-1132(Z), and HFO-1123 into hydrogen fluoride and the at least one member selected from the group consisting of HFO-1132(E), HFO-1132(Z), and HFO-1123. This method involves distillation separation using the properties of HFO-1132(E), HFO-1132(Z), or HFO-1123 and hydrogen fluoride becoming an azeotrope-like composition.

This separation method is preferably used to separate a composition that comprises HFO-1132(E) and hydrogen fluoride into HFO-1132(E) and hydrogen fluoride, to separate a composition that comprises HFO-1132(Z) and hydrogen fluoride into HFO-1132(Z) and hydrogen fluoride, and to separate a composition that comprises HFO-1123 and hydrogen fluoride into HFO-1123 and hydrogen fluoride.

The small amount of HF extracted together as an azeotrope-like composition can be recovered using other general-purpose methods (absorption by water) in combination, whereby the loss can be minimized, and the burden on the equipment can be reduced. Each compound and HF can all be reused as starting materials for the reaction by using a recovery method of HF without using water, such as absorption by $H_2SO_4$, or extraction or extractive distillation with the addition of a third component. The use of extraction, extractive distillation, or the like can minimize the equipment for recovery using corrosive $H_2SO_4$, and thus can reduce equipment costs.

As described above, the separation method according to the present disclosure is capable of efficiently separating hydrogen fluoride.

The embodiments are described above; however, it will be understood that various changes in forms and details can be made without departing from the spirit and scope of the claims.

Item 2. The azeotrope-like composition according to Item 1, wherein the HFO-1132 is trans-1,2-difluoroethylene (HFO-1132(E)).

Item 3. The azeotrope-like composition according to Item 1, wherein the HFO-1132 is cis-1,2-difluoroethylene (HFO-1132(Z)).

Item 4. The azeotrope-like composition according to Item 2, having a boiling point of −40° C. to 40° C. at a pressure of 185 kPa to 2480 kPa.

Item 5. The azeotrope-like composition according to Item 3, having a boiling point of −40° C. to 40° C. at a pressure of 51 kPa to 1880 kPa.

Item 6. The azeotrope-like composition according to any one of Items 1 to 5, comprising 1,2-difluoroethylene (HFO-1132), hydrogen fluoride, and an additional compound, the additional compound being at least one member selected from the group consisting of 1,1-difluoroethylene (HFO-1132a), 1,1,2-trifluoroethylene (HFO-1123), fluoromethane (HFC-41), 1,1,2,2-tetrafluoroethane (HFC-134), and 1,1,2-trifluoroethane (HFC-143).

Item 7. An azeotrope-like composition comprising 1,1,2-trifluoroethylene (HFO-1123) and hydrogen fluoride.

Item 8. The azeotrope-like composition according to Item 7, having a boiling point of −40° C. to 40° C. at a pressure of 249 kPa to 3480 kPa.

Item 9. A separation method of a composition comprising hydrogen fluoride and at least one member selected from the group consisting of trans-1,2-difluoroethylene (HFO-1132 (E)), cis-1,2-difluoroethylene (HFO-1132(Z)), and 1,1,2-trifluoroethylene (HFO-1123), the method comprising steps (a) and (b), and optionally further comprising step (c):

(a) supplying a composition comprising hydrogen fluoride and at least one member selected from the group consisting of HFO-1132(E), HFO-1132(Z), and HFO-1123 to a first distillation column;

(b) obtaining, as a first distillate, an azeotrope-like composition comprising hydrogen fluoride and at least one member selected from the group consisting of HFO-1132(E), HFO-1132(Z), and HFO-1123, and extracting, as a bottom composition of the first distillation column, a composition that is more enriched in either i) at least one member selected from the group consisting of HFO-1132(E), HFO-1132(Z), and HFO-1123, or ii) hydrogen fluoride, in terms of the concentration, than the supplied composition; and (c) supplying the first distillate to a second distillation column to perform distillation in the second distillation column under a pressure different from that of the first distillation column.

EXAMPLES

The present disclosure is described in more detail below with reference to Examples. However, the present disclosure is not limited to the Examples.

Example 1

Tables 1 to 3 show vapor-liquid equilibrium data for mixtures of HFO-1132(E), HFO-1132(Z), or HFO-1123 with hydrogen fluoride (HF) at 40° C. The numerical units in the tables for each compound in the liquid phase and gas phase are molar ratios (in each of the liquid phase and the gas phase, the total number of moles of each compound and HF is defined as 1).

TABLE 1

| Liquid phase HFO-1132(E) molar ratio | Gas phase HFO-1132(E) molar ratio | Total pressure (MPa) |
| --- | --- | --- |
| 0.05 | 0.728 | 0.80 |
| 0.10 | 0.797 | 1.10 |
| 0.20 | 0.841 | 1.43 |
| 0.30 | 0.865 | 1.62 |
| 0.40 | 0.884 | 1.75 |
| 0.50 | 0.900 | 1.86 |
| 0.60 | 0.915 | 1.96 |
| 0.70 | 0.930 | 2.06 |
| 0.80 | 0.947 | 2.16 |
| 0.90 | 0.968 | 2.27 |
| 0.95 | 0.982 | 2.33 |
| 0.98 | 0.992 | 2.37 |
| 0.99 | 0.996 | 2.39 |

TABLE 2

| Liquid phase HFO-1132(Z) molar ratio | Gas phase HFO-1132(Z) molar ratio | Total pressure (MPa) |
| --- | --- | --- |
| 0.05 | 0.620 | 0.56 |
| 0.10 | 0.719 | 0.77 |
| 0.20 | 0.795 | 1.03 |
| 0.30 | 0.836 | 1.20 |
| 0.40 | 0.865 | 1.33 |
| 0.50 | 0.888 | 1.43 |
| 0.60 | 0.908 | 1.52 |
| 0.70 | 0.927 | 1.60 |
| 0.80 | 0.947 | 1.69 |
| 0.90 | 0.970 | 1.78 |
| 0.95 | 0.983 | 1.83 |

TABLE 2-continued

| Liquid phase HFO-1132(Z) molar ratio | Gas phase HFO-1132(Z) molar ratio | Total pressure (MPa) |
| --- | --- | --- |
| 0.98 | 0.993 | 1.86 |
| 0.99 | 0.996 | 1.88 |

TABLE 3

| Liquid phase HFO-1123 molar ratio | Gas phase HFO-1123 molar ratio | Total pressure (MPa) |
| --- | --- | --- |
| 0.05 | 0.831 | 1.32 |
| 0.10 | 0.870 | 1.80 |
| 0.20 | 0.896 | 2.25 |
| 0.30 | 0.911 | 2.50 |
| 0.40 | 0.922 | 2.67 |
| 0.50 | 0.932 | 2.81 |
| 0.60 | 0.940 | 2.92 |
| 0.70 | 0.949 | 3.04 |
| 0.80 | 0.960 | 3.17 |
| 0.90 | 0.975 | 3.32 |
| 0.95 | 0.985 | 3.40 |
| 0.98 | 0.993 | 3.46 |
| 0.99 | 0.996 | 3.48 |

Table 1 shows that a composition of HFO-1132(E) and HF becomes an azeotrope-like composition when it comprises 97 mol % or more (99 mass % or more) and less than 100 mol % of HFO-1132(E).

Table 2 shows that a composition of HFO-1132(Z) and HF becomes an azeotrope-like composition when it comprises 97 mol % or more (99 mass % or more) and less than 100 mol % of HFO-1132(Z).

Table 3 shows that a composition of HFO-1123 and HF becomes an azeotrope-like composition when it comprises 97 mol % or more (99 mass % or more) and less than 100 mol % of HFO-1123.

Accordingly, the cases in which in the vapor-liquid equilibrium data at 40° C., HFO-1132(E), HFO-1132(Z), and HFO-1123 are each present in an amount of 97 mol % or more and less than 100 mol % in a composition with HF correspond to the case in which the difference between the bubble point vapor pressure and the dew point vapor pressure of each of these compositions at 40° C. is 3% or less, indicating that these compositions were azeotrope-like compositions.

The above results demonstrate that HFO-1132(E), HFO-1132(Z), and HFO-1123 each form an azeotrope-like composition with HF. These compositions serve as important compositions in separation of HF using a distillation column.

An azeotrope-like composition comprising HFO-1132(E) and/or HFO-1132(Z), hydrogen fluoride (HF), and an additional compound that is at least one member selected from the group consisting of HFO-1132a, HFO-1123, HFC-41, HFC-134, and HFC-143 is a useful and preferable composition for separation into HFO-1132(E) and/or HFO-1132(Z), HF, and the additional compound.

Further, the difference between the bubble point vapor pressure and dew point vapor pressure of the following compositions at a specific temperature was 3% or less: the composition comprising HFO-1132(E), HF, and HFO-1132a; the composition comprising HFO-1132(E), HF, and HFO-1123; the composition comprising HFO-1132(E), HF, and HFC-41; the composition comprising HFO-1132(E), HF, and HFC-134; and the composition comprising HFO-1132(E), HF, and HFC-143.

Example 2: Method for Separating HFO-1132(E) and Hydrogen Fluoride

FIG. 1 is a diagram showing an example of a separation method using an azeotrope-like composition. Table 4 shows the flow rates of HFO-1132(E) and hydrogen fluoride at S11, S12, and S13 in FIG. 1. For the distillation column C1, the operating pressure was 1.01 MPa, the column top temperature was 7.9° C., and the column bottom temperature was 98.1° C.

From S11, a composition comprising HFO-1132(E) and hydrogen fluoride is supplied to the distillation column C1. From S13, an azeotrope-like composition comprising HFO-1132(E) and hydrogen fluoride flows out, and HFO-1132(E) with a reduced concentration of hydrogen fluoride is obtained. A small amount of hydrogen fluoride remaining in S13 can be removed by water washing, adsorption, absorption, or other methods as necessary. From S12, substantially only hydrogen fluoride is obtained, which is recycled in the reaction step.

In the system of HFO-1132(Z) and HF, and the system of HFO-1123 and HF as well, these components can be separated by azeotropic distillation in a manner similar to the above and recycled in the reaction step.

TABLE 4

|  | Flow rate (kg/hr) | | |
|---|---|---|---|
|  | S11 | S12 | S13 |
| HFO1132(E) | 7.62 | 0.00 | 7.62 |
| HF | 2.38 | 2.31 | 0.07 |

The invention claimed is:

1. An azeotrope-like composition comprising hydrogen fluoride and 99 mass % or more and less than 100 mass % of 1,2-difluoroethylene (HFO-1132), based on the total amount of HFO-1132 and hydrogen fluoride, defined as 100 mass %, and an additional compound in a total amount of more than 0 mass % and 15 mass % or less based on the entire azeotrope-like composition defined as 100 mass %, the additional compound being at least one member selected from the group consisting of 1,1-difluoroethylene (HFO-1132a), 1,1,2-trifluoroethylene (HFO-1123), fluoromethane (HFC-41), 1,1,2,2-tetrafluoroethane (HFC-134), and 1,1,2-trifluoroethane (HFC-143).

2. The azeotrope-like composition according to claim 1, wherein the HFO-1132 is trans-1,2-difluoroethylene (HFO-1132(E)).

3. The azeotrope-like composition according to claim 1, wherein the HFO-1132 is cis-1,2-difluoroethylene (HFO-1132(Z)).

4. An azeotrope-like composition comprising 1,1,2-trifluoroethylene (HFO-1123), hydrogen fluoride, and an additional compound,
the composition comprising the additional compound in a total amount of more than 0 mass % and 1 mass % or less based on the entire azeotrope-like composition defined as 100 mass %.

5. A separation method of a composition consisting of hydrogen fluoride and at least one member selected from the group consisting of trans-1,2-difluoroethylene (HFO-1132(E)), cis-1,2-difluoroethylene (HFO-1132(Z)), and 1,1,2-trifluoroethylene (HFO-1123),
the method comprising steps (a) and (b), and optionally further comprising step (c):
(a) supplying a composition comprising hydrogen fluoride and at least one member selected from the group consisting of HFO-1132(E), HFO-1132(Z), and HFO-1123 to a first distillation column;
(b) obtaining, as a first distillate, an azeotrope-like composition comprising hydrogen fluoride and at least one member selected from the group consisting of HFO-1132(E), HFO-1132(Z), and HFO-1123, and extracting, as a bottom composition of the first distillation column, a composition that is more enriched in either i) at least one member selected from the group consisting of HFO-1132(E), HFO-1132(Z), and HFO-1123, or ii) hydrogen fluoride in terms of the concentration than the supplied composition; and
(c) supplying the first distillate to a second distillation column to perform distillation in the second distillation column under a pressure different from that of the first distillation column.

* * * * *